(12) United States Patent
Rissmann et al.

(10) Patent No.: US 7,181,274 B2
(45) Date of Patent: Feb. 20, 2007

(54) METHODS FOR INDUCING FIBRILLATION UTILIZING SUBCUTANEOUS ELECTRODES

(75) Inventors: William J. Rissmann, Coto de Caza, CA (US); Gust H. Bardy, Seattle, WA (US); Riccardo Cappato, Ferrara (IT)

(73) Assignee: Cameron Health, Inc., San Clemente, CA (US)

( * ) Notice: Subject to any disclaimer, the term of this patent is extended or adjusted under 35 U.S.C. 154(b) by 127 days.

(21) Appl. No.: 10/984,392

(22) Filed: Nov. 9, 2004

(65) Prior Publication Data

US 2005/0137625 A1 Jun. 23, 2005

Related U.S. Application Data

(60) Division of application No. 10/011,533, filed on Nov. 5, 2001, now abandoned, and a continuation-in-part of application No. 09/940,471, filed on Aug. 27, 2001, now Pat. No. 7,076,296, which is a continuation-in-part of application No. 09/663,607, filed on Sep. 18, 2000, now Pat. No. 6,721,597, and a continuation-in-part of application No. 09/663,606, filed on Sep. 18, 2000, now Pat. No. 6,647,292.

(51) Int. Cl.
*A61N 1/39* (2006.01)
*A61N 1/362* (2006.01)
*A61N 1/375* (2006.01)

(52) U.S. Cl. .......................................... 607/5
(58) Field of Classification Search ........... None
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |

(Continued)

FOREIGN PATENT DOCUMENTS

DE 298 01 807 U1 7/1998

(Continued)

OTHER PUBLICATIONS

Bardy, Gust H. et al., "Multicenter Experience with a Pectoral Unipolar Implantable Cardioverter-Defibrillator," *JACC*, Aug. 1996, vol. 28, No. 2, pp. 400-410.

(Continued)

*Primary Examiner*—Kristen Mullen
(74) *Attorney, Agent, or Firm*—Crompton, Seager & Tufte, LLC

(57) ABSTRACT

A power supply for an implantable cardioverter-defibrillator for subcutaneous positioning between the third rib and the twelfth rib and for providing cardioversion/defibrillation energy to the heart, the power supply comprising a capacitor subsystem for storing the cardioversion/defibrillation energy for delivery to the patient's heart; and a battery subsystem electrically coupled to the capacitor subsystem for providing electrical energy to the capacitor subsystem.

16 Claims, 13 Drawing Sheets

U.S. PATENT DOCUMENTS

| | | |
|---|---|---|
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Wielders et al. |
| 4,567,900 A | 2/1986 | Moore |
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,800,883 A | 1/1989 | Winstrom |
| 4,830,005 A | 5/1989 | Woskow |
| 4,944,300 A | 7/1990 | Saksena |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,215,081 A | 6/1993 | Ostroff |
| 5,230,337 A | 7/1993 | Dahl et al. |
| 5,255,692 A | 10/1993 | Neubauer et al. |
| 5,261,400 A | 11/1993 | Bardy |
| 5,300,106 A | 4/1994 | Dahl et al. |
| 5,313,953 A | 5/1994 | Yomtov et al. |
| 5,331,966 A | 7/1994 | Bennett et al. |
| 5,342,407 A | 8/1994 | Dahl et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,537 A | 5/1995 | Munshi et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,439,485 A | 8/1995 | Mar et al. |
| 5,447,521 A | 9/1995 | Anderson et al. |
| 5,476,503 A | 12/1995 | Yang |
| 5,509,923 A | 4/1996 | Middleman et al. |
| 5,509,928 A | 4/1996 | Acken |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,323 A * | 7/1997 | Kroll et al. .................. 607/2 |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,766,226 A | 6/1998 | Pedersen |
| 5,776,169 A | 7/1998 | Schroeppel |
| 5,814,090 A | 9/1998 | Latterell et al. |
| 5,827,326 A | 10/1998 | Kroll et al. |
| 5,836,976 A | 11/1998 | Min et al. |
| 5,843,132 A | 12/1998 | Ilvento |
| 5,895,414 A | 4/1999 | Sanchez-Zambrano |
| 5,904,705 A | 5/1999 | Kroll et al. |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 6,006,133 A | 12/1999 | Lessar et al. |
| 6,014,586 A | 1/2000 | Weinberg et al. |
| 6,026,325 A | 2/2000 | Weinberg et al. |
| 6,058,328 A | 5/2000 | Levine et al. |
| 6,093,173 A | 7/2000 | Balceta et al. |
| 6,095,987 A | 8/2000 | Shmulewitz et al. |
| H1905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | KenKnight |
| 6,185,450 B1 | 2/2001 | Seguine et al. |
| 6,187,028 B1 | 2/2001 | Munshi |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,283,985 B1 | 9/2001 | Harguth et al. |
| 6,334,071 B1 | 12/2001 | Lu |
| 6,345,198 B1 | 2/2002 | Mouchawar et al. |
| 6,411,844 B1 | 6/2002 | Kroll et al. |
| 6,647,292 B1 | 11/2003 | Bardy et al. |
| 6,721,597 B1 | 4/2004 | Bardy et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 2001/0027330 A1 | 10/2001 | Sullivan et al. |
| 2002/0035380 A1 | 3/2002 | Rissmann et al. |

FOREIGN PATENT DOCUMENTS

| | | |
|---|---|---|
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | 1 000 634 A1 | 5/2000 |
| WO | WO 00/41766 A1 | 7/2000 |
| WO | WO 00/50120 A1 | 8/2000 |

| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Higgins, Steven L. et al., "The First Year Experience with the Dual Chamber ICD," *PACE*, Jan. 2000. vol. 23, pp. 18-25.

Mirowski, M. et al., "Automatic Detection and Defibrillation of Lethal Arrhythmias—A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970, p. 1123 (single sheet).

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Schwacke, H. et al., "Komplikationen mit Sonden bei 340 Patienten mit einem Implantierbaren Kardioverter/Defibrillator," *Z Kardiol* (1999) vol. 88, No. 8, pp. 559-565.

Tietze U. et al., "Halbleiter-Schaltungstechnik" © Springer-Verlag (Berlin, Germany), (1991), pp. 784-786.

Valenzuela, Terrence D. et al., "Outcomes of Rapid Defibrillation by Security Officers After Cardiac Arrest in Casinos," *The New England Journal of Medicine*, Oct. 26, 2000, vol. 343. No. 17, pp. 1206-1209.

Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.

* cited by examiner

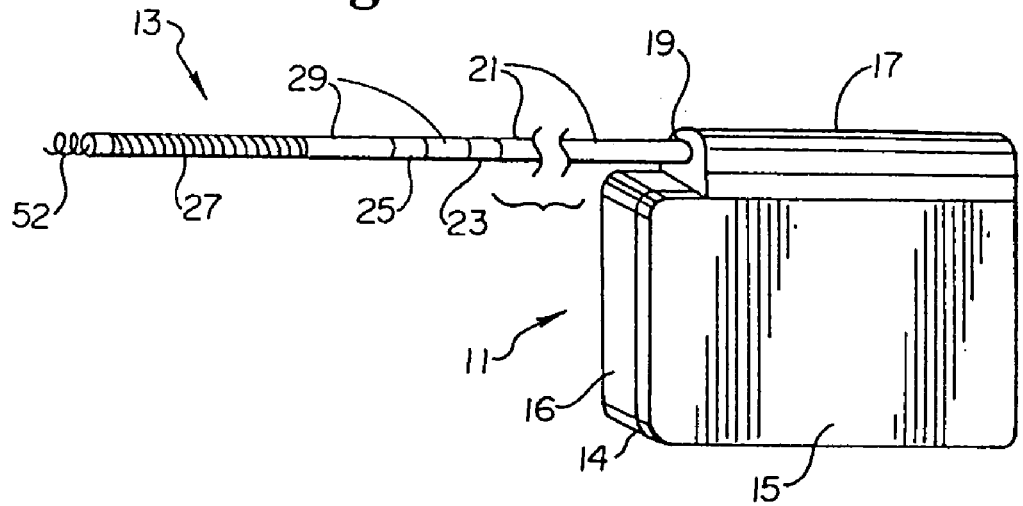
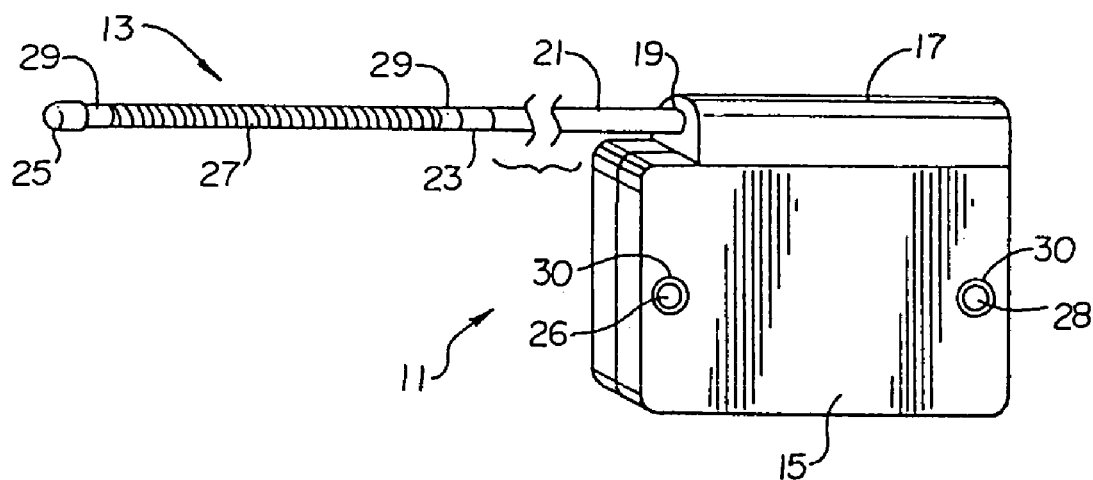
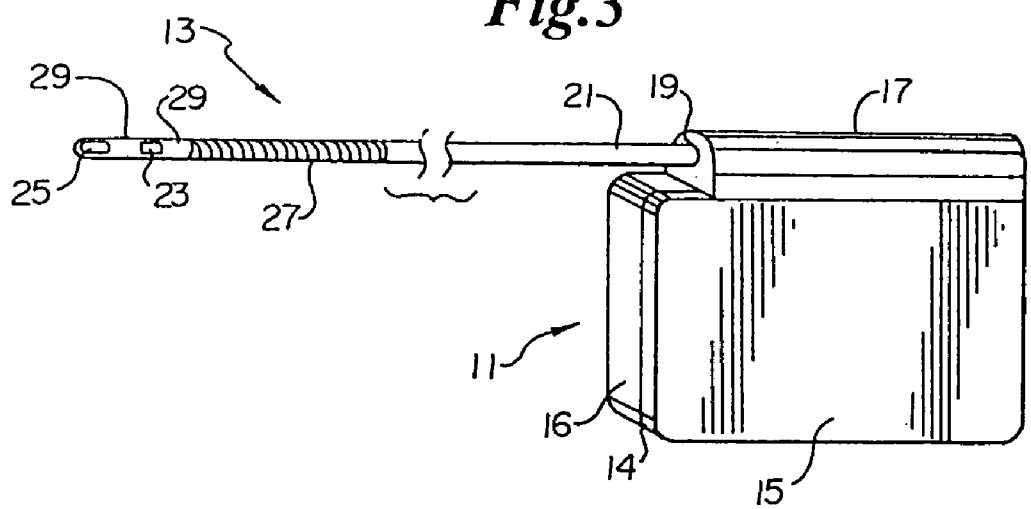

| CAPACITORS | EFFECTIVE V | EFFECTIVE C | PULSE WIDTH | INDIV C | TOTAL VOLUME |
|---|---|---|---|---|---|
| 1 | 350 V | 3380μF | 377 msec | 3380μF | 27.6 cc's |
| 2 | 700 V | 845μF | 94 msec | 1,690μF | 27.6 cc's |
| 3 | 1,050 V | 376μF | 42 msec | 1,128μF | 27.6 cc's |
| 4 | 1,400 V | 211μF | 23 msec | 844μF | 27.6 cc's |
| 5 | 1,750 V | 135μF | 15 msec | 675μF | 27.6 cc's |
| 6 | 2,100 V | 94μF | 10 msec | 564μF | 27.6 cc's |

Fig.22

CHARGE TIMES vs. POWER SUPPLY EFFICIENCY, TWO BATTERIES

| STORED ENERGY | INVERTER EFFICIENCY | TIME, BOL | TIME, EOL |
|---|---|---|---|
| 207 J | 65% | 25.5 sec | 31.8 sec |
| 207 J | 70% | 23.6 sec | 29.6 sec |
| 207 J | 75% | 22.1 sec | 27.6 sec |
| 207 J | 80% | 20.7 sec | 25.8 sec |
| 207 J | 85% | 19.5 sec | 24.3 sec |
| 207 J | 90% | 18.4 sec | 23.0 sec |

Fig.23

CHARGE TIME vs. NUMBER OF BATTERIES

| ENERGY | NUMBER BATTERIES | EFFICIENCY | TIME, BOL | TIME, EOL | NUMBER BATTERIES | TIME, BOL | TIME, EOL |
|---|---|---|---|---|---|---|---|
| 207 J | 3 | 65% | 17.0 sec | 21.2 sec | 4 | 12.7 sec | 15.9 sec |
| 207 J | 3 | 70% | 15.8 sec | 19.7 sec | 4 | 11.8 sec | 14.8 sec |
| 207 J | 3 | 75% | 14.7 sec | 18.4 sec | 4 | 11.0 sec | 13.8 sec |
| 207 J | 3 | 80% | 13.8 sec | 17.3 sec | 4 | 10.4 sec | 12.9 sec |
| 207 J | 3 | 85% | 13.0 sec | 16.2 sec | 4 | 9.7 sec | 12.2 sec |
| 207 J | 3 | 90% | 12.3 sec | 15.3 sec | 4 | 9.2 sec | 11.5 sec |

Fig.26

DEVICE WIDTH'S & LENGTH'S vs. THICKNESS

| EXAMPLE | THICKNESS | WIDTH | LENGTH | VOLUME |
|---|---|---|---|---|
| 1 | 0.2 in (0.51 cm) | 1.9 in (4.83 cm) | 8.0 in (20.32 cm) | 50 cc's |
| 2 | 0.3 in (0.76 cm) | 1.5 in (3.81 cm) | 6.8 in (17.27 cm) | 50 cc's |
| 3 | 0.4 in (1.02 cm) | 1.3 in (3.40 cm) | 6.0 in (15.24 cm) | 50 cc's |
| 4 | 0.3 in (0.76 cm) | 2.0 in (5.08 cm) | 4.6 in (11.76 cm) | 50 cc's |

Fig.27

VARIATIONS IN CAPACITORS & BATTERIES AT VARIOUS ENERGY LEVELS

| ENERGY DELIVERED | ENERGY STORED | EFFECTIVE VOLTAGE | EFFEC CAP VALUE | PULSE WIDTH 60 Ohm | # OF CAP'S | INVERT EFF'Y | WHr PER CHARGE | CHARGE TIME BOL | # OF BATT'S |
|---|---|---|---|---|---|---|---|---|---|
| 150 J | 207 J | 2,100 V | 94 µF | 10 msec | 6 | 75% | 276 | 11 sec | 4 |
| 125 J | 172 J | 1,750 V | 112 µF | 12 msec | 5 | 75% | 229 | 9 sec | 4 |
| 100 J | 137 J | 1,750 V | 89 µF | 9 msec | 5 | 75% | 183 | 10 sec | 3 |
| 75 J | 103 J | 1,400 V | 105 µF | 9 msec | 4 | 75% | 137 | 11 sec | 2 |
| 50 J | 69 J | 1,050 V | 125 µF | 10 msec | 3 | 75% | 92 | 7 sec | 2 |

METHODS FOR INDUCING FIBRILLATION UTILIZING SUBCUTANEOUS ELECTRODES

CROSS-REFERENCE TO RELATED APPLICATIONS

This application is a divisional of U.S. application Ser. No. 10/011,533, filed Nov. 5, 2001, abandoned; which is a continuation-in-part of U.S. patent application entitled "SUBCUTANEOUS ONLY IMPLANTABLE CARDIO-VERTER-DEFIBRILLATOR AND OPTIONAL PACER," having Ser. No. 09/663,607, filed Sep. 18, 2000, now U.S. Pat. No. 6,721,597; U.S. patent application entitled "UNITARY SUBCUTANEOUS ONLY IMPLANTABLE CARDIOVERTER-DEFIBRILLATOR AND OPTIONAL PACER," having Ser. No. 09/663,606, filed Sep. 18, 2000, now U.S. Pat. No. 6,647,292; and U.S. patent application entitled "POWER SUPPLY FOR AN IMPLANTABLE SUBCUTANEOUS CARDIOVERTER-DEFIBRILLATOR," having Ser. No. 09/940,471, filed Aug. 27, 2001, now U.S. Pat. No. 7,076,296, of which all applications are assigned to the assignee of the present application, and the disclosures of all applications are hereby incorporated by reference.

FIELD OF THE INVENTION

The present invention relates to an apparatus and method for performing electrical cardioversion/defibrillation and optional pacing of the heart via a totally subcutaneous non-transvenous system.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks of a magnitude substantially greater than pulses used in cardiac pacing. Shocks used for defibrillation therapy can comprise a biphasic truncated exponential waveform. As for pacing, a constant current density is desired to reduce or eliminate variability due to the electrode/tissue interface.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue or, more commonly, are on the distal regions of small cylindrical insulated catheters that typically enter the subclavian venous system, pass through the superior vena cava and into one or more endocardial areas of the heart. Such electrode systems are called intravascular or transvenous electrodes. U.S. Pat. Nos. 4,603,705; 4,693,253; 4,944,300; and 5,105,810, the disclosures of which are all incorporated herein by reference, disclose intravascular or transvenous electrodes employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in to the thorax. This system is far more complicated to use than current ICD systems using transvenous lead systems together with an active can electrode, and therefore it has no practical use. It has, in fact, never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400, 5,620,477; and 5,658,321, the disclosures of which are incorporated herein by reference.

ICDs are now an established therapy for the management of life-threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD.

Because >75% of cardiac arrests occur in the home, and over half occur in the bedroom, patients at risk of cardiac arrest are often alone or asleep and cannot be helped in time with an AED. Moreover, its success depends to a reasonable degree on an acceptable level of skill and calm by the bystander user.

What is needed therefore, especially for children and for prophylactic long-term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

SUMMARY OF THE INVENTION

A power supply for an implantable cardioverter-defibrillator for subcutaneous positioning between the third rib and the twelfth rib and for providing cardioversion/defibrillation energy to the heart, the power supply comprising a capacitor subsystem for storing the cardioversion/defibrillation energy for delivery to the patient's heart; and a battery subsystem electrically coupled to the capacitor subsystem for providing electrical energy to the capacitor subsystem.

BRIEF DESCRIPTION OF THE DRAWINGS

For a better understanding of the invention, reference is now made to the drawings where like numerals represent similar objects throughout the figures where:

FIG. 1 is a schematic view of a Subcutaneous ICD (S-ICD) of the present invention;

FIG. 2 is a schematic view of an alternate embodiment of a subcutaneous electrode of the present invention;

FIG. 3 is a schematic view of an alternate embodiment of a subcutaneous electrode of the present invention;

FIG. 22 is a table that shows several examples for the battery subsystem comprising two battery cells, as well as varying efficiencies and charge times in an embodiment of the present invention;

FIG. 23 is a table that shows several examples for the battery subsystem comprising various numbers of battery cells, efficiencies and charge times in an embodiment of the present invention;

FIG. 26 is a table that shows various examples of sizes for the combined capacitor subsystem and the battery subsystem in an embodiment of the present invention; and FIG. 27 is a table that shows several examples of the capacitor subsystem and the battery subsystem at different energy levels in an embodiment of the present invention.

DETAILED DESCRIPTION

Figure 4:
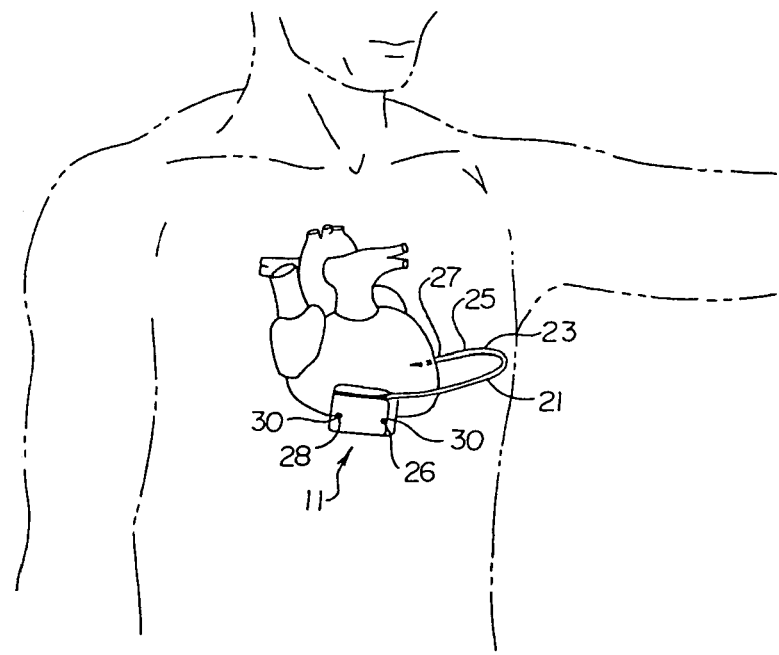
FIG. 4 is a schematic view of the S-ICD and lead of FIG. 1 subcutaneously implanted in the thorax of a patient.

Turning now to FIG. 1, the S-ICD of the present invention is illustrated. The S-ICD consisted of an electrically active canister 11 and a subcutaneous electrode 13 attached to the canister. The canister has an electrically active surface 15 that is electrically insulated from the electrode connector block 17 and the canister housing 16 via insulating area 14. The canister can be similar to numerous electrically active canisters commercially available in that the canister will contain a battery supply, capacitor and operation circuitry. Alternatively, the canister can be thin and elongated to conform to the intercostal space. The circuitry will be able to monitor cardiac rhythms for tachycardia and fibrillation, and if detected, will initiate charging the capacitor and then delivering cardioversion/defibrillation energy through the active surface of the housing and to the subcutaneous electrode. Examples of such circuitry are described in U.S. Pat. Nos. 4,693,253 and 5,105,810, the entire disclosures of which are herein incorporated by reference. The canister circuitry can provide cardioversion/defibrillation energy in different types of waveforms. In one embodiment, a 100 uF biphasic waveform is used of approximately 10–20 ms total duration and with the initial phase containing approximately ⅔ of the energy. However, any type of waveform can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the active surface and the subcutaneous electrode. Pacing stimuli will be biphasic in one embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also, the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of atrial fibrillation as described in Olson, W. et al., "Onset and Stability for Ventricular Tachyarrhythmia Detection in an Implantable Cardioverter and Defibrillator," Computers in Cardiology (1986) pp. 167–170. Detection can be provided via R—R Cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize, in its most direct form, a rate detection algorithm that triggers charging of the capacitor once the ventricular rate exceeds some predetermined level for a fixed period of time: for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R—R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patent is not respiring and this lack of respiration can be used to confirm the QRS findings of cardiac arrest. The same technique can be used to provide information about the respiratory rate or estimate cardiac output as described in U.S. Pat. Nos. 6,095,987; 5,423,326; and 4,450,527, the entire disclosures of which are incorporated herein by reference.

The canister of the present invention can be made out of titanium alloy or other presently preferred electrically active canister designs. However, it is contemplated that a malleable canister that can conform to the curvature of the patient's chest will be preferred. In this way the patient can have a comfortable canister that conforms to the shape of the patient's rib cage. Examples of conforming canisters are provided in U.S. Pat. No. 5,645,586, the entire disclosure of which is herein incorporated by reference. Therefore, the canister can be made out of numerous materials such as medical grade plastics, metals, and alloys. In the preferred embodiment, the canister is smaller than 60 cc volume having a weight of less than 100 gms for long-term wearability, especially in children. The canister and the lead of the S-ICD can also use fractal or wrinkled surfaces to increase surface area to improve defibrillation capability. Because of the primary prevention role of the therapy and the likely need to reach energies over 40 joules, a feature of the preferred embodiment is that the charge time for the therapy, is intentionally left relatively long to allow capacitor charging within the limitations of device size. Examples of small ICD housings are disclosed in U.S. Pat. Nos. 5,597,956 and 5,405,363, the entire disclosures of which are herein incorporated by reference.

Different subcutaneous electrodes 13 of the present invention are illustrated in FIGS. 1–3. Turning to FIG. 1, the lead 21 for the subcutaneous electrode is preferably composed of silicone or polyurethane insulation. The electrode is connected to the canister at its proximal end via connection port 19 which is located on an electrically insulated area 17 of the canister. The electrode illustrated is a composite electrode with three different electrodes attached to the lead. In the embodiment illustrated, an optional anchor segment 52 is attached at the most distal end of the subcutaneous electrode for anchoring the electrode into soft tissue such that the electrode does not dislodge after implantation.

The most distal electrode on the composite subcutaneous electrode is a coil electrode 27 that is used for delivering the high voltage cardioversion/defibrillation energy across the heart. The coil cardioversion/defibrillation electrode is about 5–10 cm in length. Proximal to the coil electrode are two sense electrodes, a first sense electrode 25 is located proximally to the coil electrode and a second sense electrode 23 is located proximally to the first sense electrode. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 29. Similar types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention.

One such modification is illustrated in FIG. 2 where the two sensing electrodes 25 and 23 are non-circumferential sensing electrodes and one is located at the distal end, the other is located proximal thereto with the coil electrode located in between the two sensing electrodes. In this embodiment, the sense electrodes are spaced about 6 to about 12 cm apart depending on the length of the coil electrode used. FIG. 3 illustrates yet a further embodiment where the two sensing electrodes are located at the distal end to the composite electrode with the coil electrode located proximally thereto. Other possibilities exist and are contemplated within the present invention. For example, having only one sensing electrode, either proximal or distal to the coil cardioversion/defibrillation electrode with the coil serving as both a sensing electrode and a cardioversion/defibrillation electrode.

It is also contemplated within the scope of the invention that the sensing of QRS waves (and transthoracic impedance) can be carried out via sense electrodes on the canister housing or in combination with the cardioversion/defibrillation coil electrode and/or the subcutaneous lead sensing electrode(s). In this way, sensing could be performed via the one coil electrode located on the subcutaneous electrode and the active surface on the canister housing. Another possibility would be to have only one sense electrode located on the subcutaneous electrode and the sensing would be performed by that one electrode and either the coil electrode on the subcutaneous electrode or by the active surface of the canister. The use of sensing electrodes on the canister would eliminate the need for sensing electrodes on the subcutaneous electrode. It is also contemplated that the subcutaneous electrode would be provided with at least one sense electrode, the canister with at least one sense electrode, and if multiple sense electrodes are used on either the subcutaneous electrode and/or the canister, that the best QRS wave detection combination will be identified when the S-ICD is implanted and this combination can be selected, activating the best sensing arrangement from all the existing sensing possibilities. Turning again to FIG. 2, two sensing electrodes 26 and 28 are located on the electrically active surface 15 with electrical insulator rings 30 placed between the sense electrodes and the active surface. These canister sense electrodes could be switched off and electrically insulated during and shortly after defibrillation/cardioversion shock delivery. The canister sense electrodes may also be placed on the electrically inactive surface of the canister. In the embodiment of FIG. 2, there are actually four sensing electrodes, two on the subcutaneous lead and two on the canister. In the preferred embodiment, the ability to change which electrodes are used for sensing would be a programmable feature of the S-ICD to adapt to changes in the patient physiology and size (in the case of children) over time. The programming could be done via the use of physical switches on the canister, or as presently preferred, via the use of a programming wand or via a wireless connection to program the circuitry within the canister.

The canister could be employed as either a cathode or an anode of the S-ICD cardioversion/defibrillation system. If the canister is the cathode, then the subcutaneous coil electrode would be the anode. Likewise, if the canister is the anode, then the subcutaneous electrode would be the cathode.

The active canister housing will provide energy and voltage intermediate to that available with ICDs and most AEDs. The typical maximum voltage necessary for ICDs using most biphasic waveforms is approximately 750 volts with an associated maximum energy of approximately 40 joules. The typical maximum voltage necessary for AEDs is approximately 2000–5000 volts with an associated maximum energy of approximately 200–360 joules depending upon the model and waveform used. The S-ICD of the present invention uses maximum voltages in the range of about 350 to about 3500 volts and is associated with energies of about 0.5 to about 350 joules. The capacitance of the S-ICD could range from about 25 to about 200 microfarads.

The sense circuitry contained within the canister is highly sensitive and specific for the presence or absence of life threatening ventricular arrhythmias. Features of the detection algorithm are programmable and the algorithm is focused on the detection of V-Fib and high rate V-Tach (>240 bpm). Although the S-ICD of the present invention may rarely be used for an actual life-threatening event, the simplicity of design and implementation allows it to be employed in large populations of patients at modest risk with modest cost by non-cardiac electrophysiologists. Consequently, the S-ICD of the present invention focuses mostly on the detection and therapy of the most malignant rhythm disorders. As part of the detection algorithm's applicability to children, the upper rate range is programmable upward for use in children, known to have rapid supraventricular tachycardias and more rapid ventricular fibrillation. Energy levels also are programmable downward in order to allow treatment of neonates and infants.

Turning now to FIG. 4, the optimal subcutaneous placement of the S-ICD of the present invention is illustrated. As would be evidence to a person skilled in the art, the actual location of the S-ICD is in a subcutaneous space that is developed during the implantation process. The heart is not exposed during this process and the heart is schematically illustrated in the figures only for help in understanding where the canister and coil electrode are three-dimensionally located in the left mid-clavicular line approximately at the level of the inframammary crease at approximately the 5th rib. The lead 21 of the subcutaneous electrode traverses in a subcutaneous path around the thorax terminating with its distal electrode end at the posterior axillary line ideally just lateral to the left scapula. This way the canister and subcutaneous cardioversion/defibrillation electrode provide a reasonably good pathway for current delivery to the majority of the ventricular myocardium.

Figure 5:
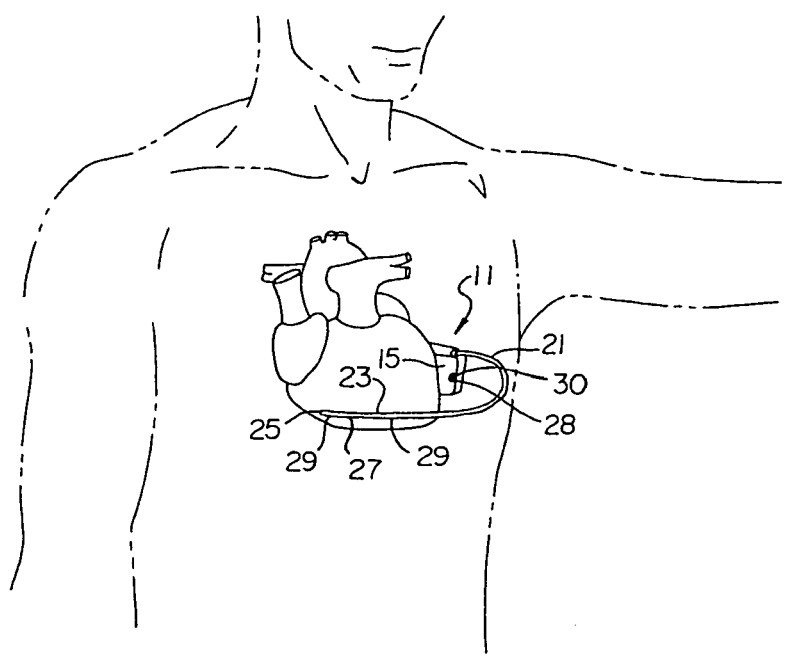
FIG. 5 is a schematic view of the S-ICD and lead of FIG. 2 subcutaneously implanted in an alternate location within the thorax of a patient.
Figure 6:
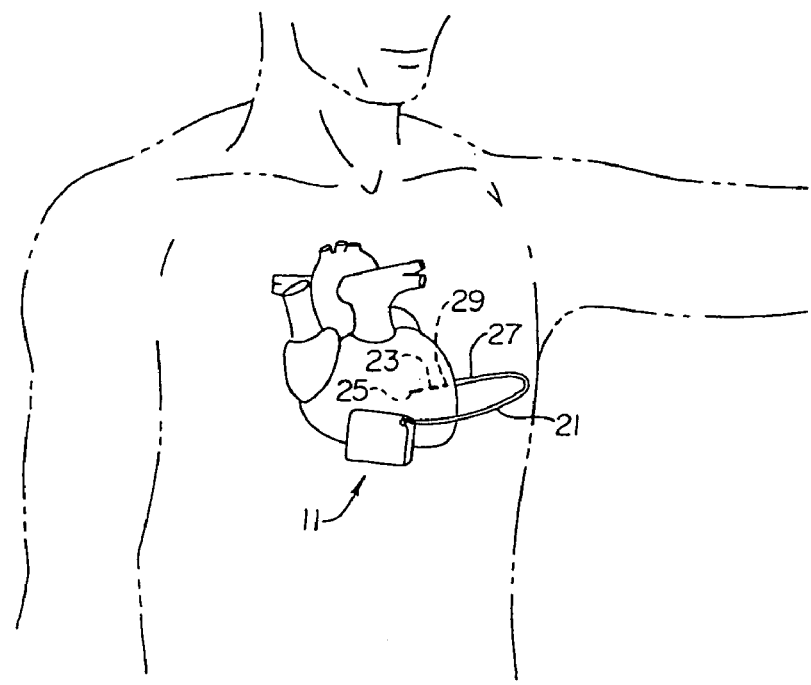
FIG. 6 is a schematic view of the S-ICD and lead of FIG. 3 subcutaneously implanted in the thorax of a patient.

FIG. 5 illustrates a different placement of the present invention. The S-ICD canister with the active housing is located in the left posterior axillary line approximately lateral to the tip of the inferior portion of the scapula. This location is especially useful in children. The lead 21 of the subcutaneous electrode traverses in a subcutaneous path around the thorax terminating with its distal electrode end at the anterior precordial region, ideally in the inframammary crease. FIG. 6 illustrates the embodiment of FIG. 1 subcutaneously implanted in the thorax with the proximal sense electrodes 23 and 25 located at approximately the left axillary line with the cardioversion/defibrillation electrode just lateral to the tip of the inferior portion of the scapula.

Figure 7:
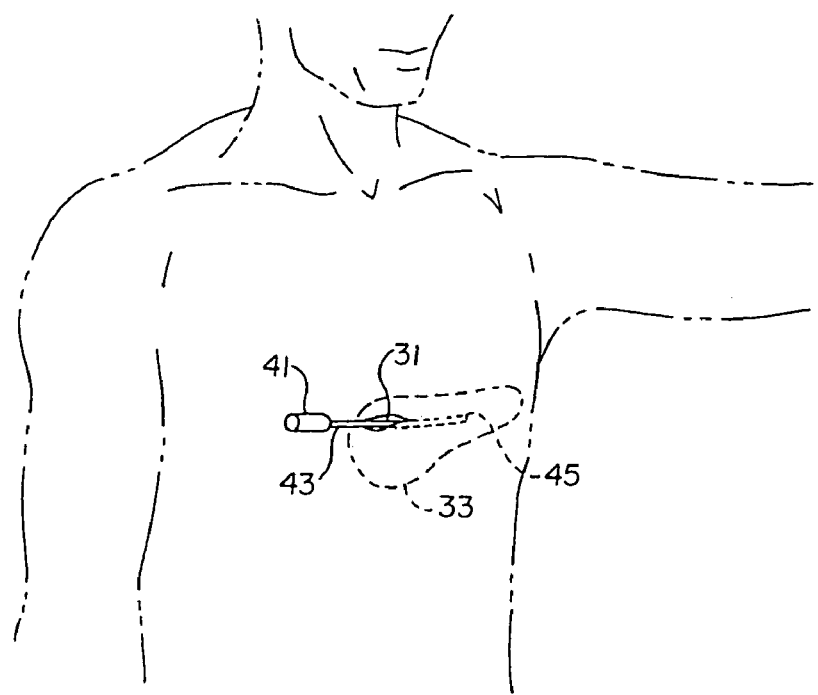
FIG. 7 is a schematic view of the method of making a subcutaneous path from the preferred incision and housing implantation point to a termination point for locating a subcutaneous electrode of the present invention.

FIG. 7 schematically illustrates the method for implanting the S-ICD of the present invention. An incision 31 is made in the left anterior axillary line approximately at the level of the cardiac apex. This incision location is distinct from that chosen for S-ICD placement and is selected specifically to allow both canister location more medially in the left inframammary crease and lead positioning more posteriorly via the introducer set (described below) around to the left posterior axillary line lateral to the left scapula. That said, the incision could be anywhere on the thorax deemed reasonable by the implanting physician although in the preferred embodiment, the S-ICD of the present invention will be applied in this region. A subcutaneous pathway 33 is then created medially to the inframammary crease for the canister and posteriorly to the left posterior axillary line lateral to the left scapula for the lead.

Figure 8:
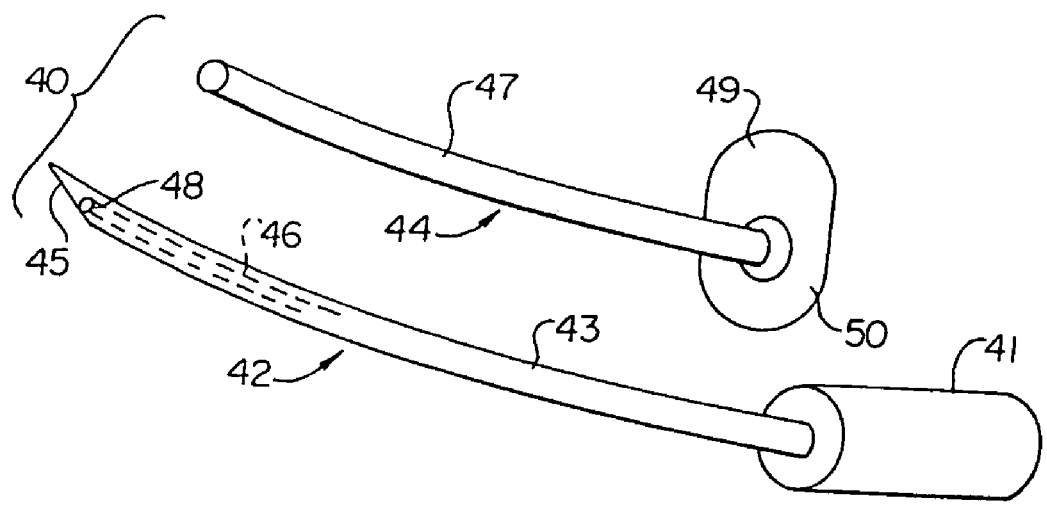
FIG. 8 is a schematic view of an introducer set for performing the method of lead insertion of any of the described embodiments.

The S-ICD canister 11 is then placed subcutaneously at the location of the incision or medially at the subcutaneous region at the left inframammary crease. The subcutaneous electrode 13 is placed with a specially designed curved introducer set 40 (see FIG. 8). The introducer set comprises a curved trocar 42 and a stiff curved peel away sheath 44. The peel away sheath is curved to allow for placement around the rib cage of the patient in the subcutaneous space created by the trocar. The sheath has to be stiff enough to allow for the placement of the electrodes without the sheath collapsing or bending. Preferably the sheath is made out of a biocompatible plastic material and is perforated along its axial length to allow for it to split apart into two sections. The trocar has a proximal handle 41 and a curved shaft 43. The distal end 45 of the trocar is tapered to allow for dissection of a subcutaneous path 33 in the patient. Preferably, the trocar is cannulated having a central lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. The curved peel away sheath 44 has a proximal pull tab 49 for breaking the sheath into two halves along its axial shaft 47. The sheath is placed over a guidewire inserted through the trocar after the subcutaneous path has been created. The subcutaneous pathway is then developed until it terminates subcutaneously at a location that if a straight line were drawn from the canister location to the path termination point the line would intersect a substantial portion of the left ventricular mass of the patient. The guidewire is then removed leaving the peel away sheath. The subcutaneous lead system is then inserted through the sheath until it is in the proper location. Once the subcutaneous lead system is in the proper location, the sheath is split in half using the pull tab 49 and removed. If more than one subcutaneous electrode is being used, a new curved peel away sheath can be used for each subcutaneous electrode.

Figure 9:
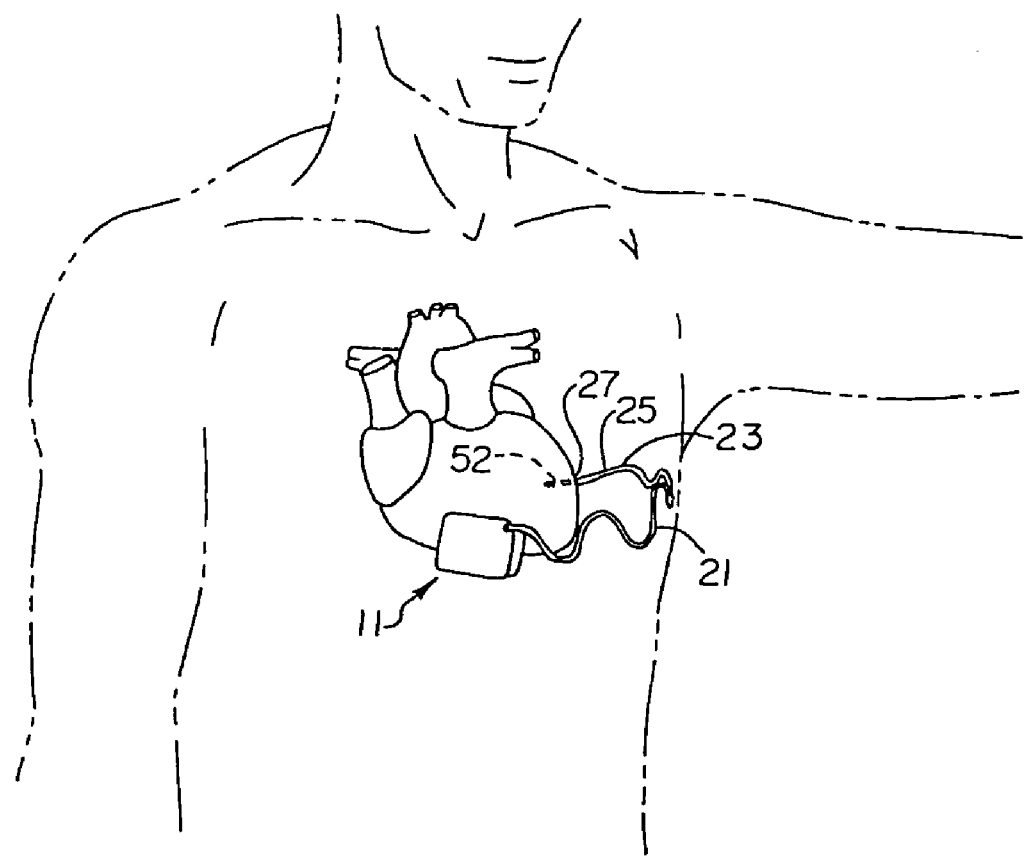
FIG. 9 is a schematic view of an alternative S-ICD of the present invention illustrating a lead subcutaneously and serpiginously implanted in the thorax of a patient for use particularly in children.

The S-ICD will have prophylactic use in adults where chronic transvenous/epicardial ICD lead systems pose excessive risk or have already resulted in difficulty, such as sepsis or lead fractures. It is also contemplated that a major use of the S-ICD system of the present invention will be for prophylactic use in children who are at risk for having fatal arrhythmias, where chronic transvenous lead systems pose significant management problems. Additionally, with the use of standard transvenous ICDs in children, problems develop during patient growth in that the lead system does not accommodate the growth. FIG. 9 illustrates the placement of the S-ICD subcutaneous lead system such that the problem that growth presents to the lead system is overcome. The distal end of the subcutaneous electrode is placed in the same location as described above providing a good location for the coil cardioversion/defibrillation electrode 27 and the sensing electrodes 23 and 25. The insulated lead 21, however, is no longer placed in a taut configuration. Instead, the lead is serpiginously placed with a specially designed introducer trocar and sheath such that it has numerous waves or bends. As the child grows, the waves or bends will straighten out, lengthening the lead system while maintaining proper electrode placement. Although it is expected that fibrous scarring especially around the defibrillation coil will help anchor it into position to maintain its posterior position during growth, a lead system with a distal tine or screw electrode anchoring system 52 can also be incorporated into the distal tip of the lead to facilitate lead stability (see FIG. 1). Other anchoring systems can also be used such as hooks, sutures, or the like.

Figure 10:
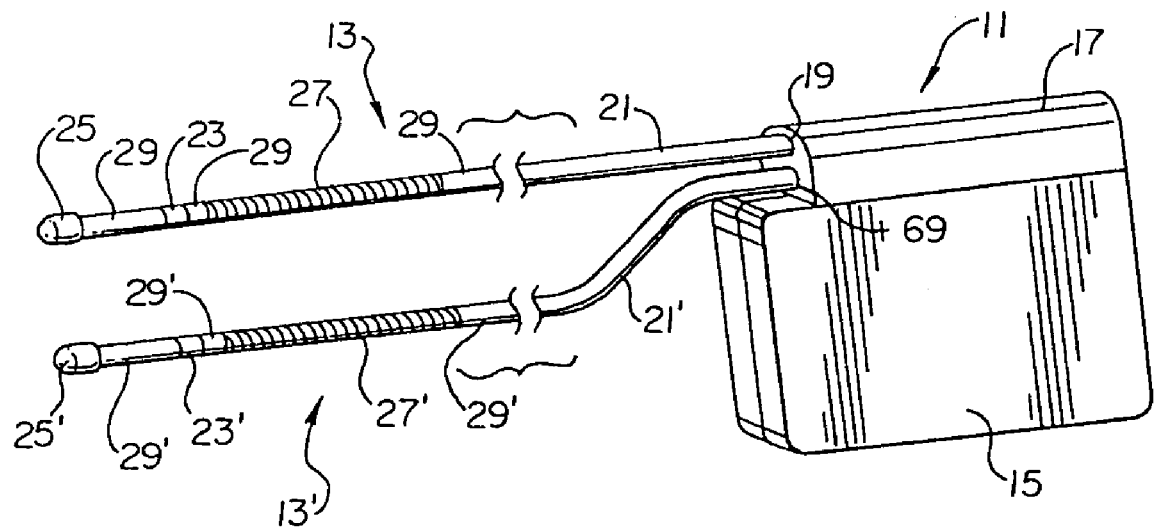
FIG. 10 is a schematic view of an alternate embodiment of an S-ICD of the present invention.
Figure 11:
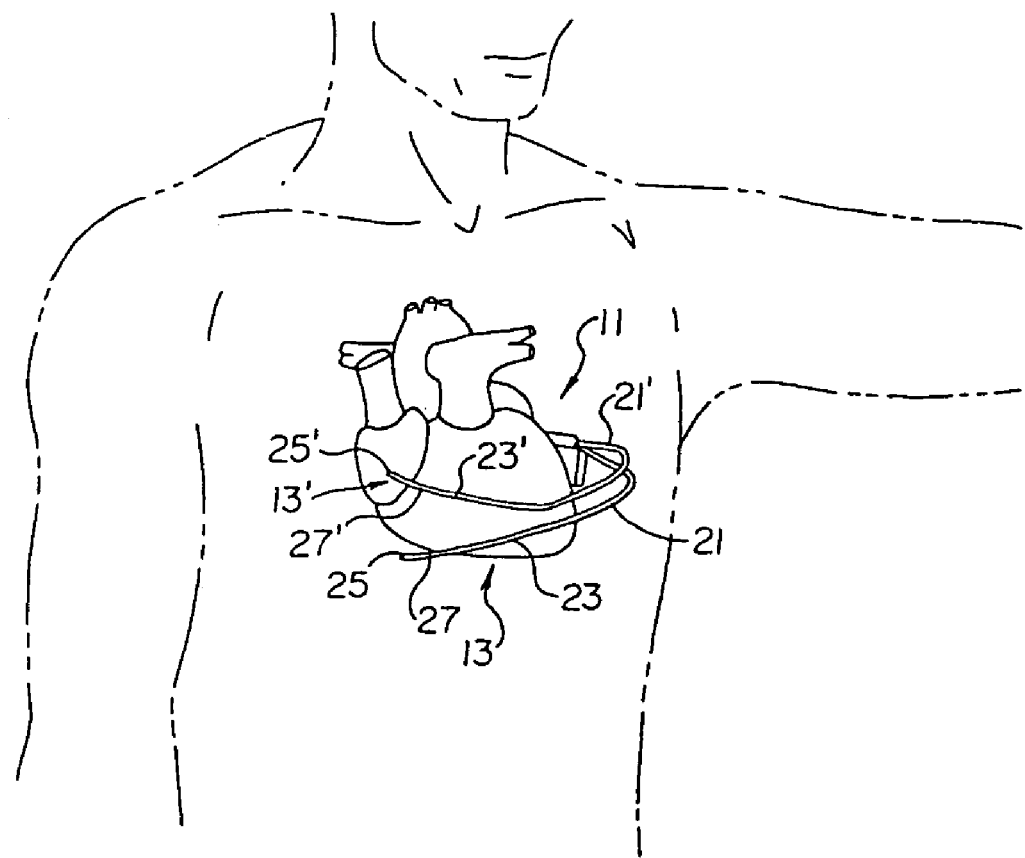
FIG. 11 is a schematic view of the S-ICD of FIG. 10 subcutaneously implanted in the thorax of a patient.

FIGS. 10 and 11 illustrate another embodiment of the present S-ICD invention. In this embodiment, there are two subcutaneous electrodes 13 and 13' of opposite polarity to the canister. The additional subcutaneous electrode 13' is essentially identical to the previously described electrode. In this embodiment, the cardioversion/defibrillation energy is delivered between the active surface of the canister and the two coil electrodes 27 and 27'. Additionally, provided in the canister is means for selecting the optimum sensing arrangement between the four sense electrodes 23, 23', 25, and 25'. The two electrodes are subcutaneously placed on the same side of the heart. As illustrated in FIG. 6, one subcutaneous electrode 13 is placed inferiorly and the other electrode 13' is placed superiorly. It is also contemplated with this dual subcutaneous electrode system that the canister and one subcutaneous electrode are the same polarity and the other subcutaneous electrode is the opposite polarity.

Figure 12:
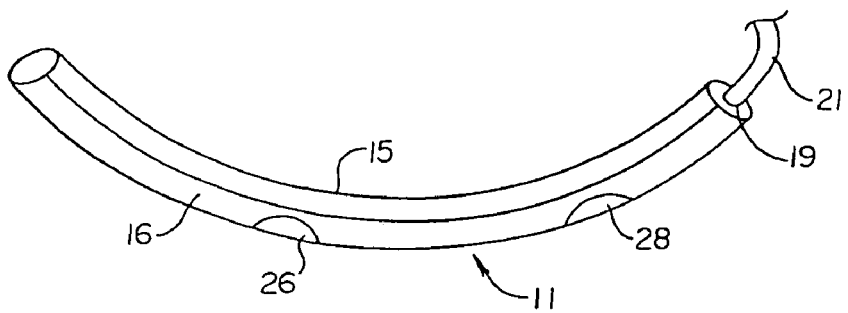
FIG. 12 is a schematic view of yet a further embodiment where the canister of the S-ICD of the present invention is shaped to be particularly useful in placing subcutaneously adjacent and parallel to a rib of a patient.
Figure 13:
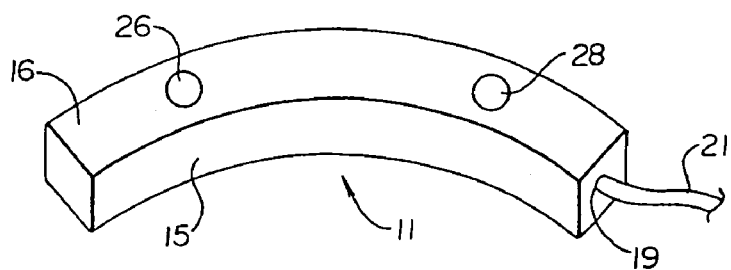
FIG. 13 is a schematic view of a different embodiment where the canister of the S-ICD of the present invention is shaped to be particularly useful in placing subcutaneously adjacent and parallel to a rib of a patient.

Turning now to FIGS. 12 and 13, further embodiments are illustrated where the canister 11 of the S-ICD of the present invention is shaped to be particularly useful in placing subcutaneously adjacent and parallel to a rib of a patient. The canister is long, thin, and curved to conform to the shape of the patient's rib. In the embodiment illustrated in FIG. 12, the canister has a diameter ranging from about 0.5 cm to about 2 cm with 1 cm being presently preferred. Alternatively, instead of having a circular cross-sectional area, the canister could have a rectangular or square cross-sectional area as illustrated in FIG. 13 without falling outside of the scope of the present invention. The length of the canister can vary depending on the size of the patient's thorax. Currently, the canister is about 5 cm to about 15 cm long with about 10 being presently preferred. The canister is curved to conform to the curvature of the ribs of the thorax. The radius of the curvature will vary depending on the size of the patient, with smaller radiuses for smaller patients and larger radiuses for larger patients. The radius of the curvature can range from about 5 cm to about 35 cm depending on the size of the patient. Additionally, the radius of the curvature need not be uniform throughout the canister such that it can be shaped closer to the shape of the ribs. The canister has an active surface 15 that is located on the interior (concave) portion of the curvature and an inactive surface 16 that is located on the exterior (convex) portion of the curvature. The leads of these embodiments, which are not illustrated except for the attachment port 19 and the proximal end of the lead 21, can be any of the leads previously described above, with the lead illustrated in FIG. 1 being presently preferred.

The circuitry of this canister is similar to the circuitry described above. Additionally, the canister can optionally have at least one sense electrode located on either the active surface or the inactive surface and the circuitry within the canister can be programmable as described above to allow for the selection of the best sense electrodes. It is presently preferred that the canister have two sense electrodes 26 and 28 located on the inactive surface of the canisters as illustrated, where the electrodes are spaced from about 1 to about 10 cm apart with a spacing of about 3 cm being presently preferred. However, the sense electrodes can be located on the active surface as described above.

It is envisioned that the embodiment of FIG. 12 will be subcutaneously implanted adjacent and parallel to the left anterior 5th rib, either between the 4th and 5th ribs or between the 5th and 6th ribs. However, other locations can be used.

Another component of the S-ICD of the present invention is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacings to optimize signal detection comparable to the implantable system.

FIGS. 14 to 18 depict particular US-ICD embodiments of the present invention. The various sensing, shocking and pacing circuitry, described in detail above with respect to the S-ICD embodiments, may additionally be incorporated into the following US-ICD embodiments. Furthermore, particular aspects of any individual S-ICD embodiment discussed above may be incorporated, in whole or in part, into the US-ICD embodiments depicted in the following figures.

Figure 14:
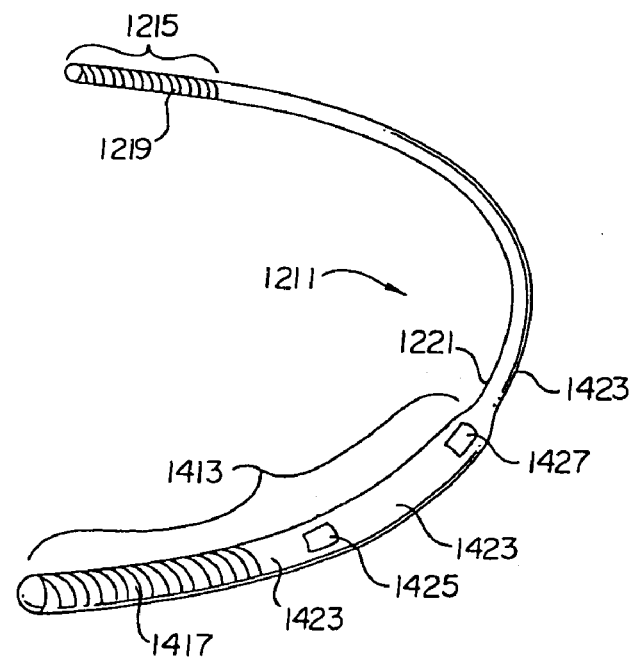
FIG. 14 is a schematic view of a Unitary Subcutaneous ICD (US-ICD) of the present invention.

Turning now to FIG. 14, the US-ICD of the present invention is illustrated. The US-ICD consists of a curved housing 1211 with a first and second end. The first end 1413 is thicker than the second end 1215. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillating electrodes 1417 and 1219 located on the outer surface of the two ends of the housing. The circuitry can provide cardioversion/defibrillation energy in different types of waveforms. In one embodiment, a 100 uF biphasic waveform is used of approximately 10–20 ms total duration and with the initial phase containing approximately ⅔ of the energy. However, any type of waveform can be utilized such as monophasic, biphasic, multiphasic or alternative waveforms as is known in the art.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way the patient can have a comfortable canister that conforms to the unique shape of the patient's rib cage. Examples of conforming ICD housings are provided in U.S. Pat. No. 5,645,586, the entire disclosure of which is herein incorporated by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 joules, a feature of the preferred embodiment is that the charge time for the therapy intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide with about 1 cm being presently preferred. As microtechnology advances, the thickness of the housing will become smaller.

The two cardioversion/defibrillation electrodes on the housing are used for delivering the high voltage cardioversion/defibrillation energy across the heart. In the preferred embodiment, the cardioversion/defibrillation electrodes are coil electrodes. However, other cardioversion/defibrillation electrodes could be used such as having electrically isolated active surfaces or platinum alloy electrodes. The coil cardioversion/defibrillation electrodes are about 5–10 cm in length. Located on the housing between the two cardioversion/defibrillation electrodes are two sense electrodes 1425 and 1427. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 1423. Analogous types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister or, as presently preferred, via the use of a programming wand or via a wireless connection to program the circuitry within the canister.

Figure 15:
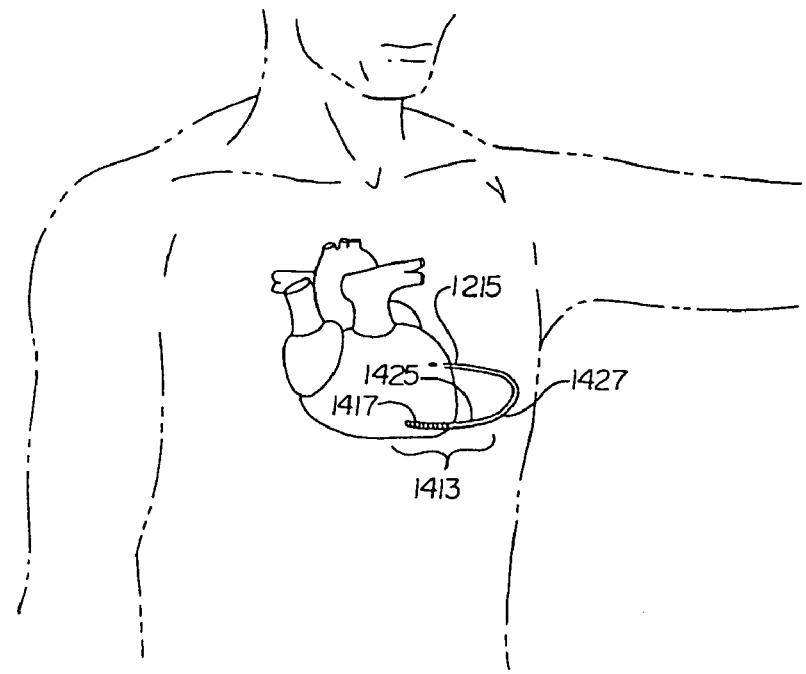
FIG. 15 is a schematic view of the US-ICD subcutaneously implanted in the thorax of a patient.

Turning now to FIG. 15, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the figures only for help in understanding where the device and its various electrodes are three-dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 16:
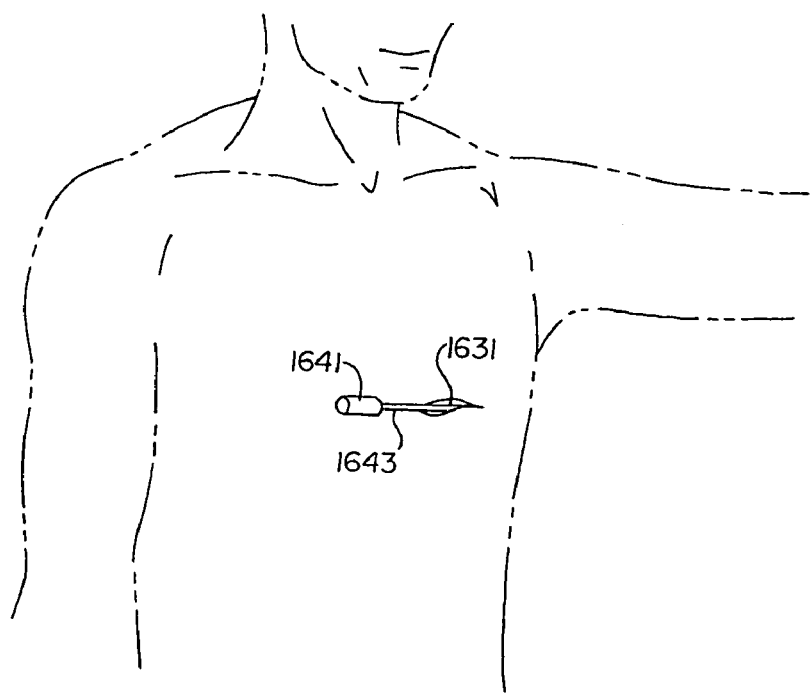
FIG. 16 is a schematic view of the method of making a subcutaneous path from the preferred incision for implanting the US-ICD.
Figure 17:
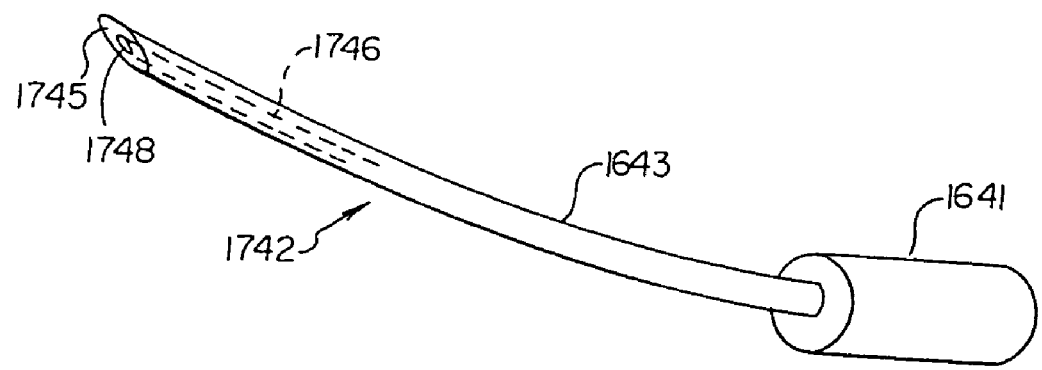
FIG. 17 is a schematic view of an introducer for performing the method of US-ICD implantation.

FIG. 16 schematically illustrates the method for implanting the US-ICD of the present invention. An incision 1631 is made in the left anterior axillary line approximately at the level of the cardiac apex. A subcutaneous pathway is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway is created medially to the inframammary crease and extends posteriorly to the left posterior axillary line. The pathway is developed with a specially designed curved introducer 1742 (see FIG. 17). The trocar has a proximal handle 1641 and a curved shaft 1643. The distal end 1745 of the trocar is tapered to allow for dissection of a subcutaneous path in the patient. Preferably, the trocar is cannulated having a central lumen 1746 and terminating in an opening 1748 at the distal end. Local anesthetic such as lidocaine can be delivered, if necessary, through the lumen or through a curved and elongated needle designed to anesthetize the path to be used for trocar insertion should general anesthesia not be employed. Once the subcutaneous pathway is developed, the US-ICD is implanted in the subcutaneous space, the skin incision is closed using standard techniques.

Figure 18:
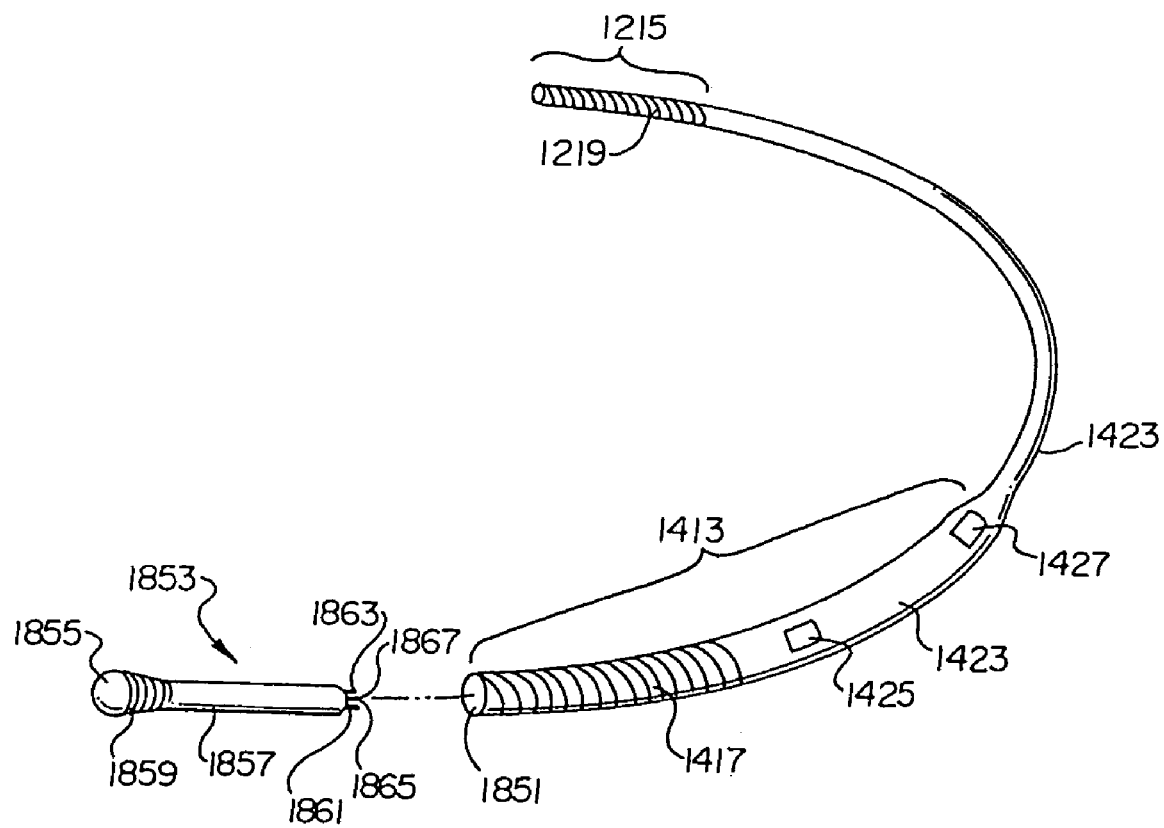
FIG. 18 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 18, a different embodiment is schematically illustrated in exploded view which provides different sized US-ICDs that are easier to manufacture. The different sized US-ICDs will all have the same sized and shaped thick end 1413. The thick end is hollow inside allowing for the insertion of a core operational member 1853. The core member comprises a housing 1857 which contains the battery supply, capacitor and operational circuitry for the US-ICD. The proximal end of the core member has a plurality of electronic plug connectors. Plug connectors 1861 and 1863 are electronically connected to the sense electrodes via pressure fit connectors (not illustrated) inside the thick end which are standard in the art. Plug connectors 1865 and 1867 are also electronically connected to the cardioverter/defibrillator electrodes via pressure fit connectors inside the thick end. The distal end of the core member comprises an end cap 1855, and a ribbed fitting 1859 which creates a water-tight seal when the core member is inserted into opening 1851 of the thick end of the US-ICD.

The core member of the different sized and shaped US-ICD will all be the same size and shape. That way, during an implantation procedure, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

Figure 19:
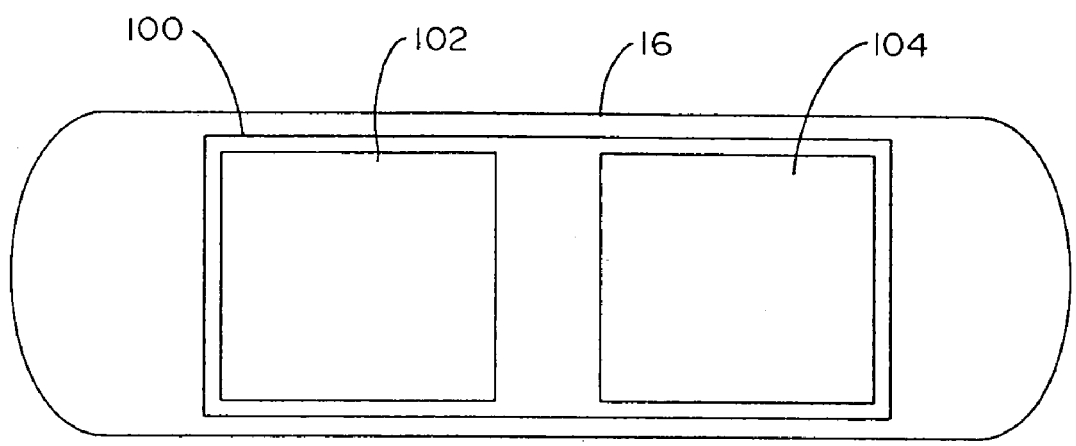
FIG. 19 is a block diagram showing the power supply of an implantable cardioverter/defibrillator in an embodiment according to the present invention.

A block diagram of a power supply 100 for use in an S-ICD device of the present invention is shown in FIG. 19. The power supply 100 is located in canister housing 16 and comprises a capacitor subsystem 102 electrically coupled to a battery subsystem 104. In an embodiment, the battery subsystem 104 comprises one or more individual battery cell(s) and the capacitor subsystem 102 comprises one or more individual capacitor(s).

In certain embodiments of the present invention, it is desirable to position the canister housing 16 in close proximity to the patient's heart, without directly contacting the heart or the intrathoracic blood vessels. In one embodiment, the canister housing 16 placement is just over the patient's ribcage.

In operation, the battery subsystem 104 provides electrical energy to charge up the capacitor subsystem 102. After charge-up, the capacitor subsystem 102 delivers the cardioversion/defibrillation energy to the patient's heart through the electrodes. In one embodiment, the power supply 100 can provide approximately 0.5 to approximately 350 joules of cardioversion/defibrillation energy to the heart through approximately 60 ohms of thoracic impedance.

A procedure to determine the composition of the capacitor subsystem 102 and the battery subsystem 104 will now be described. Generally, the approach to determine needed capacitor values includes considerations for the internal impedance of the capacitors. As a result of this internal impedance, not all of the energy stored by the capacitors will be delivered due to the inherent inefficiencies of the capacitors. Thus, it is often necessary to work backwards from the desired energy delivered in order to calculate the needed capacitor values.

Generally, the procedure to determine the proper capacitor values of the present invention includes the following steps: determine the amount of cardioversion/defibrillation energy required to be delivered to the patient's heart; determine the amount of energy lost due to truncation of the energy waveform; determine the amount of energy that must be stored in the capacitor subsystem 102 by considering the amount of energy loss from the internal impedance of the capacitor subsystem 102; determine the effective capacitor value of the capacitor subsystem 102 associated with using different amounts of individual capacitors; calculate the physical volume of the different numbers of individual capacitors for placement on a circuit board; and determine the pulse width for each of the effective capacitor values.

The first step is to determine the amount of energy that must be delivered to a patient's heart to provide an effective cardioversion/defibrillation therapy. In addition, the effective energy levels incorporate critical information regarding the associated voltage, current, waveform duration and tilt for effective cardioversion/defibrillation. Use of the term "energy" throughout this description automatically incorporates these other waveform characteristics. Because this information has not been available heretofore, this data can be acquired by performing, for example, human or animal studies to determine the appropriate levels of the energy.

Next, it is common industry practice to truncate the trailing edge of a capacitor-based cardioversion/defibrillation waveform because the trailing edge can often produce undesirable side effects, such as creating pro-arrhythmic currents should it persist too long. Thus, the amount of energy delivered can be calculated by the formula:

$$E_{STORED} = E_{DEL}/T,$$

where $E_{STORED}$ is the maximum amount of energy by the capacitor, $E_{DEL}$ is the amount of energy delivered to the heart and T is the truncation percentage of the waveform.

In order to determine the amount of energy as shown above, the amount of energy stored in the capacitors is typically compensated for by considering the internal impedance of the capacitor subsystem 102, which is known as the Effective Series Resistance ("ESR"). In addition, the ratio of delivered energy to stored energy is often expressed as the capacitor efficiency.

After calculation of the energy stored by the capacitor subsystem 102, the actual values of the individual capacitor(s) can be determined. The amount of energy stored by an individual capacitor is given by the formula:

$$E = \frac{1}{2}[C(V)^2],$$

where E is the total amount of energy stored by a capacitor, C is the amount of capacitance and V is the amount of voltage for each individual capacitor. From this equation, it can be seen that a number of tradeoffs exist in determining the capacitor value(s) to achieve the desired cardioversion/defibrillation output, including the individual capacitor value(s) and the voltage across each individual capacitor(s). For example, considerations may include voltages of commercially available capacitors as well as specific capacitor values most appropriate for cardioversion/defibrillation therapy.

It is also noted from the equation above that larger voltages permit smaller values of capacitors in order to obtain the same energy level. The voltage is constrained, however, by the voltage limitation of each individual capacitor. Often, in order to produce voltages required for cardioversion/defibrillation, a series connection of capacitors may be implemented to allow these higher overall output voltages, while at the same time keeping each individual capacitor's voltage below its maximum rating. Examples of embodiments of the present invention when considering these factors are shown in greater detail below.

Typically, the value for each individual capacitor, $C_{IND}$ is determined first for the capacitor subsystem 102. Next, the effective capacitance of the capacitor subsystem 102, $C_{EFF}$, can be determined from the equation above. Solving for $C_{EFF}$, the equation above becomes $C_{EFF} = 2 \times E/(V)^2$.

Finally, once the individual capacitor values(s) have been determined, the physical volume for each of the individual capacitor(s) can also be determined. In order to solve for volume of the individual capacitors, the equation is used as follows:

$$V_{IND} = E/\text{volumetric density},$$

where $V_{IND}$ is the individual capacitor volume, E is the stored energy, and the volumetric density is measured in joules/cubic centimeters. Under multiple capacitor scenarios, individual capacitor volumes can be summed to determine the total volume due to the capacitors. Specifically, the total device volume can be determined by the equation $E_{TOTAL} = (\text{the number of capacitors}) \times V_{IND}$.

Derivation of the equation used to determine pulse width depends on the amount of cardioversion/defibrillation energy delivered by the capacitor subsystem 102. In addition, the pulse width must be truncated or the pulse width will stretch indefinitely because of the exponential nature of the components. Specifically, the amount of energy delivered by the capacitor subsystem 102 can be determined by the fact that the amount of energy left in the capacitor subsystem 102, $E_{FINAL}$, is equal to the amount of the energy initially stored in the capacitor subsystem 102, $E_{INIT}$, minus the amount of energy delivered by the shock, $E_{DEL}$. In addition, the amount of energy stored in the capacitor subsystem 102 after a shock, $E_{FINAL}$, is also defined by the equation as follows:

$$E_{FINAL} = \tfrac{1}{2}[C_{EFF}][V_{FINAL}]^2 = \tfrac{1}{2}[C_{EFF}][V_{INIT}][e^{-\tau/R C_{EFF}}]^2,$$

where $\tau$ is the pulse width and R is the impedance of the body.

After calculating the makeup of the capacitor subsystem 104, the composition of the battery subsystem 102 of the present invention can be determined. First, the total amount of energy for the battery subsystem 104 that is required to provide a maximum number of energy shocks at a certain amount of energy delivered is determined. Next, after considering the overall efficiency of the battery subsystem 102, the total amount of energy for this number of energy shocks is calculated. Finally, the total physical volume and effective lifetime of the battery subsystem 102 can be determined.

Based on the calculations described above, several examples of embodiments of the capacitor subsystem 102 and the battery subsystem 104 will now be shown. As an example of an embodiment of the present invention, the power supply 100 may provide approximately 150 joules of energy to be delivered to the heart. Further, in an embodiment, the waveform of the energy delivered to the heart will be truncated at approximately 97%. Therefore, in this example, the energy output of the capacitor, $E_{OUT}$, will equal to 150 joules divided by the truncation level 97%, or 155 joules.

In an embodiment, the efficiency of the energy stored in the capacitor is approximately 75%. With an energy output of the capacitor equal to 155 joules, the stored energy will be 155 joules divided by the efficiency 75% or 207 joules.

The effective capacitance $C_{EFF}$ can now be calculated using the equation $C_{EFF} = 2 \times E/(V)_2$. In this example, assuming E is approximately 207 joules and V is approximately 350 volts, $C_{EFF}$ is approximately 3,380 microfarads. Because the individual capacitance, $C_{IND}$, equals the number of capacitors times the effective capacitance, $C_{EFF}$, the individual capacitance of the single capacitor also is approximately 3,380 microfarads.

In order to solve for physical volume, the equation $V_{IND} = E/\text{volume metric density}$ is used. In this example, it is assumed that the individual capacitors have a volumetric efficiency of approximately 7.5 joules/cubic centimeters for stored energy and approximately 5.5 joules/cubic centimeters for delivered energy. Therefore, in this example, individual capacitor volume, $V_{IND} = 207$ joules/7.5 joules/cubic centimeters=27.6 cubic centimeters. Further, because the capacitor volume is determined by the number of capacitors times $V_{IND}$, in this example with one individual capacitor, the total capacitor device, $V_{TOT} = 27.6$ cubic centimeters.

Finally, the value of the pulse width can be determined. In this example, $E_{FINAL} = E_{INIT} - E_{DEL} = 155.0 - 150.0 = 5.0$ joules. In addition, using the equation $E_{FINAL} = \tfrac{1}{2}[C_{EFF}][V_{FINAL}]^2 = \tfrac{1}{2}[C_{EFF}][V_{INIT}][e^{-\tau/RC_{EFF}}]^2$, the pulse width $\tau$ is equal to 377 milliseconds.

Figures 20, 21:
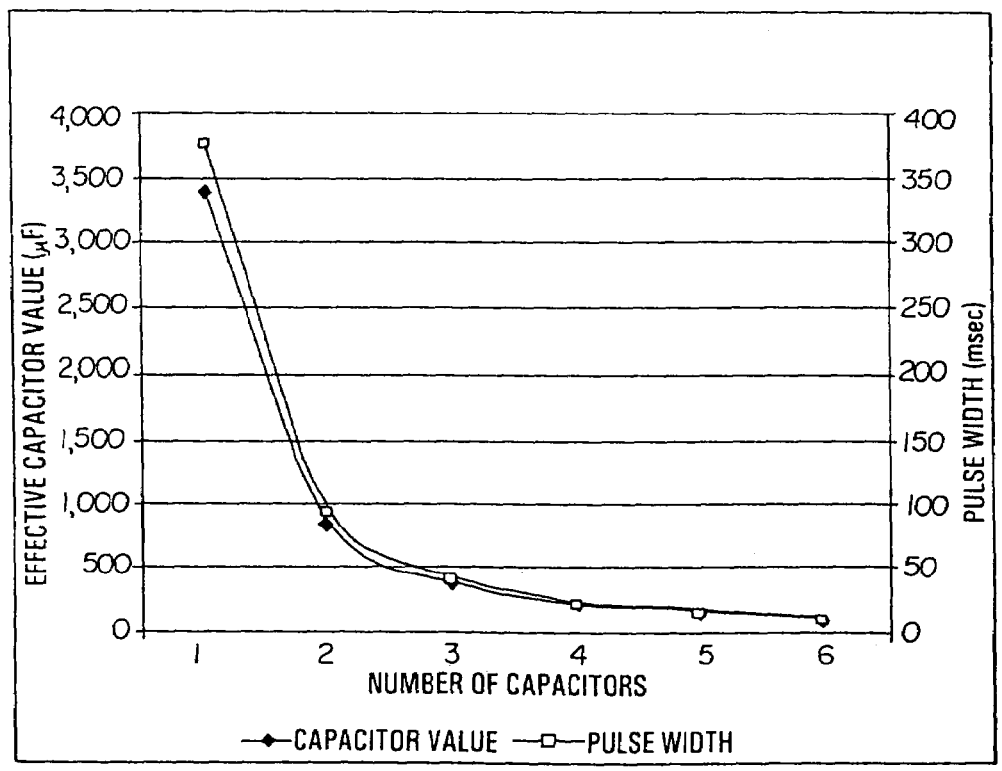
FIG. 20 is a table that shows several examples of embodiments of the present invention comprising various numbers of capacitors and pulse widths.
FIG. 21 is a graph that shows several examples of embodiments of the present invention comprising various numbers of capacitors and pulse widths.

As shown in the table in FIG. 20, several examples of embodiments of the power supply 100 of the present invention are shown to depending upon the number of capacitors and the pulse width of the energy signal delivered. In addition, FIG. 21 shows in graphical form the tabular data shown in FIG. 20.

Next, it is desired to determine the size of the battery subsystem 104 required given a maximum number of energy shocks at a certain amount of energy delivered. In this example, it is assumed that the system is capable of delivering approximately 100 maximum energy shocks at approximately 207 joules of energy. Accordingly, because 207 joules of energy is equal to 207 watt-seconds, 100 max energy shocks is equal to 20,700 watt-seconds, or 5.75 watt-hours. Assuming for this example that the power supply efficiency is approximately 65%, this yields a battery capacity requirement of 8.8 watt-hours.

In one embodiment of the present invention, the battery cells can comprise LiSVO or LiMnO$_2$ batteries that can operate for either defibrillation or monitoring requirements. In another embodiment, LiSVO or LiMnO$_2$ batteries can be employed for defibrillation operations, and LiI$_2$ or LiCFx batteries can be employed for monitoring operations.

In this example, the LiSVO batteries have an energy storage capacity of approximately ½ watt-hour/cubic centimeters per battery. Therefore, a physical volume of approximately 18 cubic centimeters of battery is required to provide 100 maximum energy shocks at approximately 207 joules of energy.

Another variable relates to time required for the battery subsystem 102 to fully charge the capacitor subsystem 104. Because batteries tend to degrade over the life of the cells, the charge time at the beginning of battery life ("BOL") is less than the end of battery life ("EOL"). The amount of charge time is equal to the power output divided by the applied battery voltage at the BOL times the maximum current. As an example, assuming a single shock of approximately 207 joules at a 65% efficiency that yields a power output of approximately 318 joules, and an applied battery voltage of approximately 5 volts at BOL and maximum current drain of approximately 2.5 amps, the battery subsystem 102 can charge the capacitor subsystem 104 in approximately 25 seconds. In this example, assuming the applied battery voltage decrease to approximately 4 volts at EOL with a current drain of approximately 2.5 amps, the battery subsystem can charge the capacitor subsystem 104 in approximately 32 seconds.

Finally, in order to determine the effective lifetime of the battery subsystem 102 assuming no shocks and no pacing, the amount of battery capacity (8.8 watt-hours) must be divided by the amount of monitoring current (15 microamps) times the total voltage (10.0 volts) times the battery efficiency (90%). For this example, the battery subsystem has an effective lifetime of approximately 65,185 hours, or 7.4 years.

In an embodiment, commercially available capacitors and batteries meeting the specifications described above are manufactured and sold by Wilson Greatbatch, Limited, of 10,000 Wehrle Dr., Clarence, N.Y. 14031. In an embodiment, the capacitor subsystem 104 can comprise film, aluminum electrolytic or wet tantalum capacitor(s). In an embodiment, the battery subsystem can comprise LiSVO, magnesium or thin film battery(ies).

FIG. 22 is a table that shows several examples for the battery subsystem 102 comprising two battery cells, as well as varying efficiencies and charge times. In addition, FIG. 23 is a table that shows several examples for the battery subsystem 102 comprising other numbers of battery cells, efficiencies and charge times.

Figure 24:
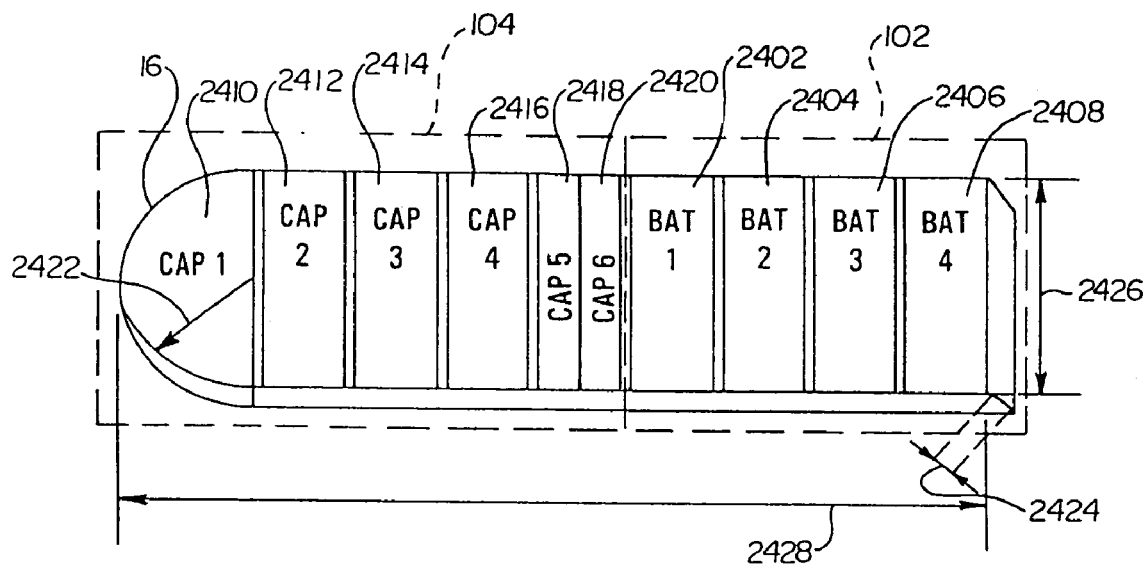
FIG. 24 is a diagram that shows one example of a physical layout for the battery subsystem and the capacitor subsystem in an embodiment of the present invention.

FIG. 24 is a diagram that shows one example of a physical layout for the battery subsystem 102 and the capacitor subsystem 104 in an embodiment of the present invention. As shown in FIG. 24, battery subsystem 102 may comprise battery cells 2402, 2404, 2406 and 2408. Capacitor subsystem 104 may comprise capacitors 2410, 2412, 2414, 2416, 2418 and 2420. Both the battery subsystem 102 and the capacitor subsystem 104 are located in the canister housing 16. In this example, it is assumed that the thickness 2424 of the canister housing 16 will be approximately 0.2 inches. As determined in the example above, each of the six capacitors 2410, 2412, 2414, 2416, 2418 and 2420 can occupy approximately 4.6 cubic centimeters of physical volume. In this example, it is noted that capacitor 2410 is substantially a half-circle in shape. Because volume is equal to area times thickness 2424 and assuming the device is 0.2 inches thick, the radius 2422 of the half-circle capacitor 16 is approximately 0.95 inches. Next, because the width 2426 is equal to twice the radius 2422, the width 2426 is approximately 1.9 inches. Then, assuming the width 2426 is approximately 1.9 inches, the thickness 2424 is approximately 0.2 inches and the volume of each of the capacitors 2412, 2414, 2416, 2418 and 2420 is approximately 4.6 cubic centimeters, each of the individual capacitors is approximately 0.74 inches in length. Therefore, the capacitor subsystem 104 is approximately 4.6 inches in length.

As for the battery subsystem 102, assuming approximately 4.5 cubic centimeters of volume per battery, the same width 2426 and thickness 2424, the length of each of the battery cells 2402, 2404, 2406 and 2408 is approximately 0.72 inches for a total of approximately 2.9 inches. Thus, the length 2428 of the canister housing 16 is approximately 4.6 inches (capacitor subsystem 104) plus 2.9 inches (battery subsystem 102) or a total of approximately 7.5 inches. Similarly, multiplying the length 2428 times the width 2426 times the thickness 2424 provides a total volume in this example of approximately 50 cubic centimeters including a provision for the electronics.

Figure 25:
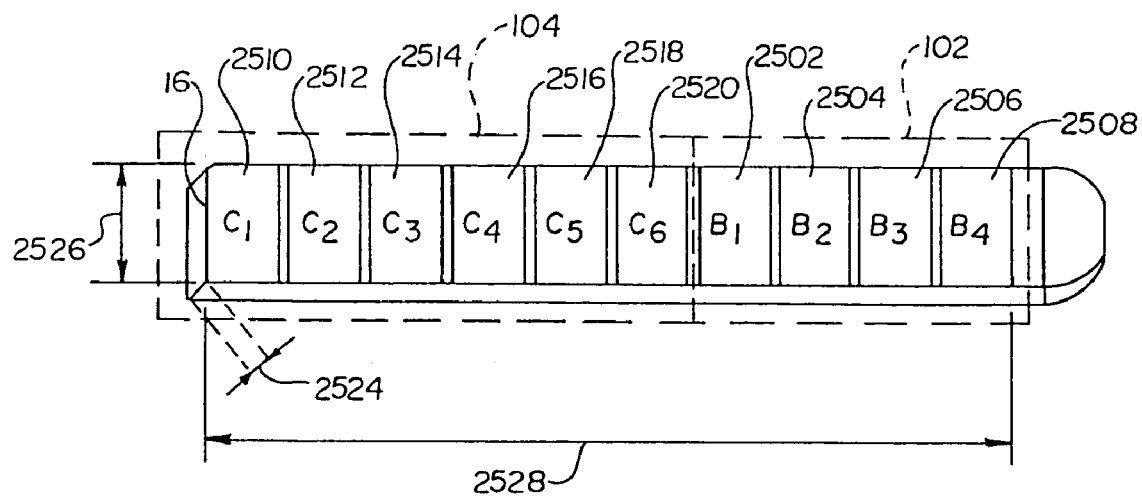
FIG. 25 shows one example of a physical layout for the battery subsystem 102 and the capacitor subsystem 104 in an embodiment of the present invention.

FIG. 25 shows one example of a physical layout for the battery subsystem 102 and the capacitor subsystem 104 in an embodiment of the present invention. AS shown in FIG. 25, battery subsystem 102 may comprise battery sells 2502, 2504, 2506 and 2508. Capacitor subsystem 104 may comprise capacitors 2510, 2512, 2514, 2516, 2518 and 2520. Both the battery subsystem 102 and the capacitor subsystem 104 are located in the canister housing 16. In this example, it is assumed that thickness 2524 of the canister housing 16 is approximately 0.3 inches. As determined in the example above, each of the six capacitors 2510, 2512, 2514, 2516, 2518 and 2520 will occupy approximately 4.6 cubic centimeters of physical volume. Assuming a width 2526 of approximately 2.0 inches, the length of each of the capacitors 2510, 2512, 2514, 2516, 2518 and 2520 is approximately 0.47 inches, and the total length of the capacitor subsystem 104 is approximately 2.8 inches. Next, given the same assumptions for the thickness 2524 and the width 2526, and that the volume of each of the battery cells 2502, 2504, 2506 and 2508 is approximately 4.5 cubic centimeters (as calculated above), each of the battery cells 2502, 2504, 2506 and 2508 is approximately 0.46 inches. Thus, the length of the battery subsystem 102 is approximately 1.8 inches and the length 2528 of the combined capacitor subsystem 104 and the battery subsystem 102 is approximately 2.8 inches plus 1.8 inches, or 4.6 inches. Further, the total volume of the capacitor subsystem 104 and the battery subsystem 102 is approximately 50 cubic centimeters.

FIG. 26 shows a table with various examples of sizes for the combined capacitor subsystem 104 and the battery subsystem 102. More specifically, the table shows various thicknesses, widths and lengths, and which all have the same volume of approximately 50 cubic centimeters. There are, of course, many variations to these potential embodiments shown in FIG. 26.

Finally, FIG. 27 shows a table of several embodiments of the capacitor subsystem 104 and the battery subsystem 102 at different energy levels. In these examples, energy levels of 150, 125, 100, 75 and 50 joules are shown. Typically, the amount of delivered energy can range from approximately 0.5 joules to approximately 350 joules. Also, in an embodiment, the peak voltage of the energy can range from approximately 350 volts to approximately 3150 volts. In addition, in these examples, a nominal effective capacitance of 100 microfarads is targeted to align with defibrillation chronaxie.

The S-ICD and US-ICD devices and methods of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing descrip-

What we claim is:

1. A method of inducing fibrillation in a patient, the method comprising providing a shock to the patient using an implanted first electrode on a lead secured to an implanted canister, the shock being provided between the first electrode and an electrode provided on the implanted canister, wherein the shock is delivered from non-vascular and non-cardiac locations.

2. The method of claim 1, further comprising providing the lead and the canister a subcutaneous locations.

3. The method of claim 2, further comprising sensing a portion of the patient's cardiac signal, and delivering the shock at a time selected for its likelihood to induce fibrillation.

4. The method of claim 3, wherein the step of sensing a portion of the patient's cardiac signal is performed using a second electrode on the lead.

5. The method of claim 1, further comprising providing the canister at the patient's left axillary line.

6. The method of claim 5, further comprising sensing a portion of the patient's cardiac signal, and delivering the shock at a time selected for its likelihood to induce fibrillation.

7. A method of inducing fibrillation of a patient's heart, the method comprising:
   providing a subcutaneous electrical device disposed exclusive of the patient's heart;
   providing a lead assembly attached to the subcutaneous electrical device such that the lead assembly does not contact the patient's heart; and
   applying an electrical signal using the subcutaneous electrical device and the lead assembly to induce ventricular fibrillation of the patient's heart; wherein:
   the lead assembly includes a first electrode;
   the subcutaneous electrical device includes a housing having a second electrode disposed thereon; and
   the step of applying an electrical signal includes providing an electrical signal between the first electrode and the second electrode.

8. The method of claim 7, further comprising sensing a portion of the patient's heart rhythm using at least one sensing electrode making up part of the lead assembly.

9. The method of claim 7, wherein the electrical signal is applied for an entire cardiac cycle of the patient's hearth.

10. The method of claim 7, wherein:
    the lead assembly includes a third electrode; and
    the method further includes the step of sensing a portion of the patient's heart rhythm using the first electrode and the third electrode as sensing electrodes.

11. The method of claim 7, further comprising:
    sensing a portion of the patient's heart rhythm; and
    determining when to apply the electrical signal using data gathered during the sensing step.

12. The method of claim 11, wherein the determining step is performed by observing the timing of a T-wave in the patient's heart rhythm.

13. The method of claim 11, wherein the determining step is performed by estimating the occurrence of a T-wave in the patient's heart rhythm.

14. A method of treating a patient susceptible to abnormal cardiac function, the method comprising:
    providing an implantable stimulus device in a patient, the implantable stimulus device including a power source and an energy storage system;
    providing a lead system for the stimulus device;
    implanting the lead system into the patient such tat the lead system does not contact the hearth;
    sensing a portion of the patient's cardiac rhythm;
    coupling the power source to the energy storage system to charge the energy storage system; and
    discharging the energy storage system using the lead system to induce fibrillation in the patient's heart; wherein the implantable stimulus device includes a first electrode disposed thereon, and the lead system includes a second electrode, wherein the step of discharging the energy storage system include discharging energy between the first electrode and the second electrode.

15. The method of claim 14, further comprising, after discharging the energy system, sensing signals generated by the patient's heart to determine whether fibrillation has been induced.

16. The method of claim 15, further comprising, if fibrillation has been induced, the steps of:
    coupling the power supply to the energy storage system to charge the energy storage system again; and
    discharging the energy storage system using the lead system to induce defibrillation.

* * * * *

UNITED STATES PATENT AND TRADEMARK OFFICE
CERTIFICATE OF CORRECTION

PATENT NO. : 7,181,274 B2  
APPLICATION NO. : 10/984392  
DATED : February 20, 2007  
INVENTOR(S) : William J. Rissmann et al.

It is certified that error appears in the above-identified patent and that said Letters Patent is hereby corrected as shown below:

Column 19  
Line 13 Claim 2, after "canister" and before "." insert -- at subcutaneous locations --.  
Line 47 Claim 9 delete "hearth", and insert therefor -- heart --.

Column 20  
Line 20 Claim 14, delete "tat", and insert therefor -- that --.  
Line 23 Claim 14, "hearth", and insert therefor -- heart --.

Signed and Sealed this

Fifteenth Day of May, 2007

JON W. DUDAS  
*Director of the United States Patent and Trademark Office*